(12) United States Patent
Nnanna et al.

(10) Patent No.: US 8,735,165 B2
(45) Date of Patent: May 27, 2014

(54) OXAZINE-BASED SENSOR FOR CONTAMINANT DETECTION, FABRICATION METHOD THEREFOR, AND USES THEREOF

(75) Inventors: Agbai Agwu Nnanna, Crown Point, IN (US); Ahmed Hasnain Jalal, Chittagong (BD)

(73) Assignee: Purdue Research Foundation, West Lafayette, IN (US)

( * ) Notice: Subject to any disclaimer, the term of this patent is extended or adjusted under 35 U.S.C. 154(b) by 40 days.

(21) Appl. No.: 13/470,728

(22) Filed: May 14, 2012

(65) Prior Publication Data

US 2012/0288953 A1 Nov. 15, 2012

Related U.S. Application Data

(60) Provisional application No. 61/485,352, filed on May 12, 2011, provisional application No. 61/507,741, filed on Jul. 14, 2011.

(51) Int. Cl.
*G01N 21/75* (2006.01)
*G01N 21/77* (2006.01)
*B05D 3/00* (2006.01)
*B05D 5/00* (2006.01)

(52) U.S. Cl.
USPC ........... 436/113; 436/165; 436/167; 436/181; 422/82.05; 422/82.11; 422/83; 422/88; 422/426; 427/162

(58) Field of Classification Search
USPC ......... 436/106, 113, 124, 164, 165, 166, 167, 436/168, 181; 422/400, 68.1, 82.05, 82.09, 422/82.11, 83, 88, 426; 427/162
See application file for complete search history.

(56) References Cited

U.S. PATENT DOCUMENTS

| | | | | |
|---|---|---|---|---|
| 4,513,087 A | * | 4/1985 | Giuliani et al. | 436/96 |
| 4,834,496 A | * | 5/1989 | Blyler et al. | 385/12 |
| 5,579,429 A | * | 11/1996 | Naum | 385/143 |
| 6,051,437 A | * | 4/2000 | Luo et al. | 436/172 |

OTHER PUBLICATIONS

Li et al. Proceedings of AWWA 2010, 2010 Annual Conference & Exposition (ACE10), Jun. 20-24, 2010, pp. 1-9.*
Chernyak et al. Sensors and Materials, vol. 2 (2), 1990, pp. 117-126.*
Jalal et al. Applied Optics, vol. 51, No. 17, Jun. 10, 2012, pp. 3768-3775.*

* cited by examiner

*Primary Examiner* — Maureen Wallenhorst
(74) *Attorney, Agent, or Firm* — Hartman Global IP Law; Gary M. Hartman; Domenica N. S. Hartman

(57) ABSTRACT

A sensor, a method for its fabrication, and a method for its use to detect contaminants, for example, ammonia, in stagnant and dynamic fluid media, especially liquid media. The sensor is an opto-chemical sensor that includes a polymer optical fiber, a sensing layer comprising oxazine 170 perchlorate on the polymer optical fiber, and a membrane layer on the sensing layer. The membrane layer is gas permeable and not permeable to the fluid in the fluid system, and moisture is entrapped by and between the sensing and membrane layers.

20 Claims, 10 Drawing Sheets

OXAZINE-BASED SENSOR FOR CONTAMINANT DETECTION, FABRICATION METHOD THEREFOR, AND USES THEREOF

STATEMENT REGARDING FEDERALLY SPONSORED RESEARCH

This invention was made with government support under Contract No. DE-FG02-05ER64131 awarded by the U.S. Department of Energy. The Government has certain rights in the invention.

CROSS REFERENCE TO RELATED APPLICATIONS

This application claims the benefit of U.S. Provisional Application Nos. 61/485,352, filed May 12, 2011, and 61/507,741, filed Jul. 14, 2011, the contents of which are incorporated herein by reference.

BACKGROUND OF THE INVENTION

The present invention generally relates to sensors and their fabrication. More particularly, this invention relates to a sensor construction and fabrication technique capable of yielding an oxazine-based sensor suitable for detecting contaminants in stagnant and dynamic fluid media.

Ammonia at elevated concentrations is poisonous to various organisms. As examples, ammonia at a level of about 22.8 ppm can be lethal to water organisms, and exposure to ammonia at levels as low as 35 ppm for more than fifteen minutes can be dangerous to human beings. Therefore, ammonia monitoring systems capable of continuous online operation are highly desired. A particular but nonlimiting example is the detection of ammonia in dynamic aqueous systems, including municipal water systems.

While various technologies have been studied for the detection of ammonia, sensors such as electro-chemical gas sensors, catalytic sensors, chemi-resistor sensors, CHEM-FET (chemical field effect transistor) sensors, and optical fiber sensors have attracted substantial attention for their ability to rapidly and continuously detect levels of gaseous phase ammonia. Among these sensors, optical fiber chemical sensors are of particular interest because they tend to be compact, light-weight, relatively inexpensive, easily multiplexed and immune to electromagnetic interference (EMI), and do not require electric power at the sensing point.

The operation of optical fiber chemical sensors is based on the ability of micro or nano-structure materials to alter their optical responses (such as reflection or absorption) in the presence of a "recognition element." Experimentation has been conducted with optical fibers and especially glass optical fiber (GOF) or optical waveguides as sensing elements. The majority of optical fiber sensor research for the detection of ammonia is believed to have been focused on the employment of GOF, and primarily focused on the detection of gaseous phase ammonia (for example, in air), and to a lesser extent the detection of liquid phase ammonia (for example, in aqueous media). GOF sensors have been developed that employ various different sensing materials, for example, polyaniline/poly(methylmethacrylate), bromocresol purple (5',5"-dibromo-o-cresolsulfophthalein)-based silica-solgel, polyaniline-based silica-core, silica solgel-based oxazine 170 perchlorate/cellulose acetate, and bromothymol blue (BTB)/ $TiO_2$ (tin oxide) films for the detection of ammonia in air. Though polymer optical fibers (POF) offer certain advantageous characteristics, for example, greater flexibility and mechanical strength as compared to GOF, it is believed that much less research has been conducted toward their use in the detection of ammonia.

Regardless of whether the intended media is gaseous (for example, air) or liquid (for example, water), a cost-effective sensor must be capable of exhibiting a high level of reversibility, which as used herein refers to the ability of a sensor to return to its initial condition with little or no hysteresis upon the removal of the analyte. GOF sensors that employ the aforementioned sensing materials have been often observed to exhibit sufficiently high hysteresis to be deemed to have poor reversibility. In contrast, optical sensors based on glass capillary tubes coated with oxazine 170 perchlorate ($C_{21}H_{22}ClN_3O_5$; CAS No. 62669-60-7) have been reported to exhibit good reversibility. A notable property of oxazine 170 perchlorate is its optical responsiveness to bandwidths of 455 to 595 nm, which allows for multiplexing. However, while various coating methods have been developed for silica-based GOF sensors, for example, dip coating, spin coating, and spray coating, available literature does not appear to indicate the successful deposition of oxazine 170 perchlorate on other optical fiber materials, for example, POF materials.

BRIEF DESCRIPTION OF THE INVENTION

The present invention provides sensors, methods for their fabrication, and methods for their use to detect contaminants, for example, ammonia, in stagnant and dynamic fluid media, especially liquid media.

According to a first aspect of the invention, a sensor is an opto-chemical sensor adapted to detect at least one contaminant in a fluid. The sensor includes a polymer optical fiber, a sensing layer comprising oxazine 170 perchlorate on the polymer optical fiber, a membrane layer on the sensing layer wherein the membrane layer is gas permeable and not permeable to the fluid in the fluid system, and moisture entrapped by and between the sensing and membrane layers.

According to a second aspect of the invention, a method is provided for fabricating an opto-chemical sensor adapted to detect at least one contaminant in a fluid. The method includes depositing a sensing layer on a polymer optical fiber wherein the sensing layer comprises oxazine 170 perchlorate, and depositing a membrane layer on the sensing layer so as to entrap moisture therebetween, wherein the membrane layer is gas permeable and not permeable to the fluid in the fluid system.

Another aspect of the invention is a method of using a sensor having the elements described above and/or fabricated using the processing steps described above.

A technical effect of the invention is that it provides a POF sensor, and particularly an oxazine 170 perchlorate-based POF evanescent sensor with the ability to sense ammonia. The invention also provides a process for the fabrication of such a POF sensor, including the deposition of oxazine 170 perchlorate and the provision of a moisture-trapping capability that ensures the functionality of oxazine 170 perchlorate-based sensors suitable for use in aqueous media. The invention also provides methods for calibration in terms of ammonia detection in both stagnant and dynamic aqueous media. Additional technical effects arise from the use of POF materials, which may offer advantages for use in applications that require the monitoring of ammonia in artificial water delivery systems, particularly if very long optical fibers are required.

Other aspects and advantages of this invention will be better appreciated from the following detailed description.

DETAILED DESCRIPTION OF THE INVENTION

Figure 1:
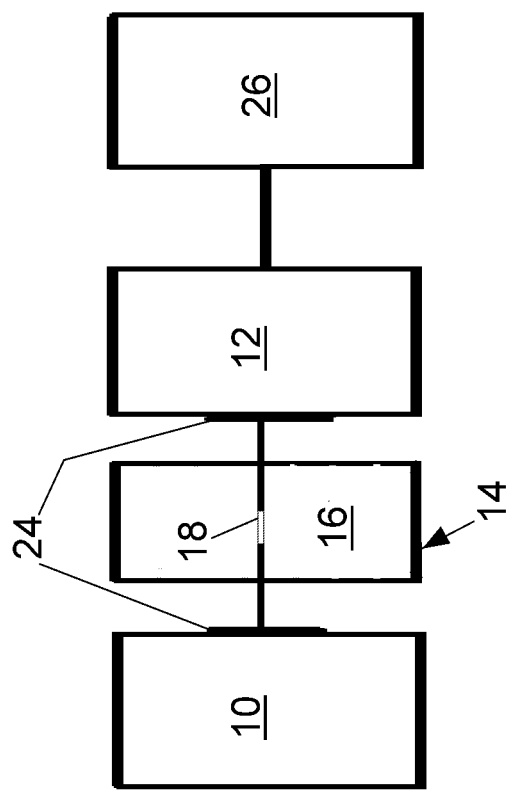
FIGS. 1 and 2 schematically represent two experimental setups employed to evaluate experimental POF-based sensors in stagnant and dynamic fluid systems.

The following describes a series of investigations leading to the development of a plastic optical fiber (POF) sensor, and particularly a POF evanescent sensor having an oxazine 170 perchlorate-based sensing layer and the ability to sense ammonia in various media, including but not limited to aqueous media. A process is also described for the fabrication of such a POF sensor, including the creation of the oxazine 170 perchlorate sensing layer and other coating layers on a POF material, and the incorporation of a moisture-trapping capability to ensure the functionality of an oxazine 170 perchlorate-based sensor for use in aqueous media. The invention also provides methods for calibration in terms of ammonia detection in both stagnant and dynamic aqueous media. Though a specific series of investigations is described below, those skilled in the art will appreciate that the invention is not necessarily limited to the particular sensor construction, sensor fabrication, and methods of use described below.

In the experimental investigations leading up to this invention, oxazine 170 perchlorate-based POF sensors were fabricated with the use of a POF material commercially available from Fiber Instrument Sales, Inc. The POF material had a poly(methyl methacrylate) (PMMA) core having a thickness of about 960 micrometers, and a fluorinated polymer cladding having a thicknesss of about 40 micrometers. POF materials constructed of these particular materials were chosen on the basis that PMMA cores readily transmit optical signals. Fluorinated polymers are known to exhibit excellent optical insulation. However, it is foreseeable that other POF materials could be used, including POF materials whose cores are other than PMMA.

Portions of the cladding layers of the POF were removed as an initial step of the fabrication process. Hydrofluoric acid (HF), sodium hydroxide (NaOH), acetone, etc., have been commonly used to de-clad GOF materials, and acetone, gas flames or lasers have been employed to de-clad POF materials. Because HF is highly corrosive and acetone and gas flames can embrittle a PMMA core and cause unevenness of deposited films, a chemical solution was devised to remove the fluorinated polymer cladding of the POF used in the investigations. The chemical solution consisted essentially of tetra hydro-furan (THF) (commercially available from, for example, FLUKA), methyl isobutyl ketone (MIBK) (commercially available from, for example, Sigma-Aldrich) and de-ionized (DI) water at a ratio of about 2:1:1. Segments of the POF having lengths of approximately 3 to 5 cm were de-clad with this solution. To reduce the risk of partial etching of the PMMA core when subjecting the POF to dipping in the chemical solution for extended periods of time, the POF segments were dipped in the solution for about one minute, after which the portion of each cladding layer that was intended to be removed was gently rubbed with lint-free lens tissues. The resulting de-cladded fiber segments were then cleaned with isopropyl alcohol and DI water several times.

To minimize optical transmission losses caused by unevenness of the de-cladded core surfaces, a polishing kit (commercially available from Thorlab) and a solution containing 70% isopropyl alcohol diluted with DI water were used to polish the etched and tip surfaces of the fiber segments. The flatness of the fiber segment tips was identified as being particularly important because light must pass through both ends of the segments with minimal scattering loss.

The de-cladded core surfaces of the fiber segments were then subjected to deposition of oxazine 170 perchlorate to form what is referred to herein as a sensing layer. For this purpose, a 0.0005 mole oxazine 170 perchlorate ($C_{21}H_{22}ClN_3O_5$) dye solution was prepared for use in a layer-by-layer dip coating process, performed in combination with a thermal treatment processing. To avoid the contamination of non-dissolved oxazine 170 perchlorate micron-sized or nano-sized particles on the fiber surfaces, supernatant of the dye solution was collected. The de-cladded core surfaces of the fiber segments were dipped into the supernatant solution while held at a temperature of about 170 to about 180° F. (about 77 to about 82° C.) until the solution was reduced to about half of its original volume. Heating of the solution was then discontinued, the coated fiber segments were allowed to cool in air for about one minute, after which the coated fiber segments were then held in the same oxazine solution for about twelve hours as the solution cooled to room temperature. Through such a process, a thin layer of oxazine 170 perchlorate having a thickness of about 20 to about 25 micrometers was deposited on the de-cladded core of each fiber segment. The thermal treatment encompassed by this process also induced a permanent U-shaped bend in the coated fiber segments.

Because oxazine 170 perchlorate is water soluble and would therefore be susceptible to dissolving in aqueous media intended for use in subsequent testing, the oxazine 170 perchlorate sensing layer was coated to have a water-impermeable membrane layer through which only a gas would be permeable. More particularly, all surfaces of the sensing layer that would be subjected to the aqueous media were covered and protected by the membrane layer. Though the use of other gas-permeable, liquid-impermeable materials is foreseeable, polydimethylsiloxane (PDMS) was employed as the membrane layer in the investigations. The PDMS membrane layer was deposited with the use of a PDMS coating solution containing a PDMS 184 silicone elastomer base and a silicone elastomer curing agent commercially available from Dow Corning.

The functionalities of oxazine 170 perchlorate as a sensing material for ammonia detection rely on the chemical reactions depicted by Equations 1-3:

$$NH_3(vapor) + H_2O \leftrightarrow NH_4^+OH^- \quad (1)$$

$$NH_4^+OH^- + H^+Dye^- \leftrightarrow NH_4^+Dye^- + H_2O \quad (2)$$

$$NH_4^+Dye^- \leftrightarrow H^+Dye^- + NH_3(vapor) \quad (3)$$

The mechanisms shown in Equations 1 through 3 suggest that the presence of moisture is necessary. Therefore, prior to deposition of the PDMS membrane layer, an additional process was performed on the fiber segments to yield a moisture-trapping layer structure on each fiber segment. In this process, the POF segments were held at room temperature for about two hours after the formation of the oxazine 170 perchlorate sensing layer. The fiber segments were then dipped in DI water for about one minute and then allowed to air dry for about one minute. During the air drying process, visible fine drops of water were removed from the fiber segments with lint-free lens tissues. Each fiber segment was then immediately dipped into the aforementioned PDMS coating solution, which was formulated to contain the PDMS 184 silicone elastomer base and the silicone elastomer curing agent at a ratio of about 10:1. The fiber segments were then hanged vertically at room temperature so that excess PDMS was removed by gravity. Curing of the PDMS membrane layer occurred over a period of about two to three days, and the resulting PDMS membrane layers had thicknesses of about 130 to about 145 micrometers. As a result of this process, moisture was entrapped by and between the sensing and membrane layers on the fiber segments.

Figure 2:
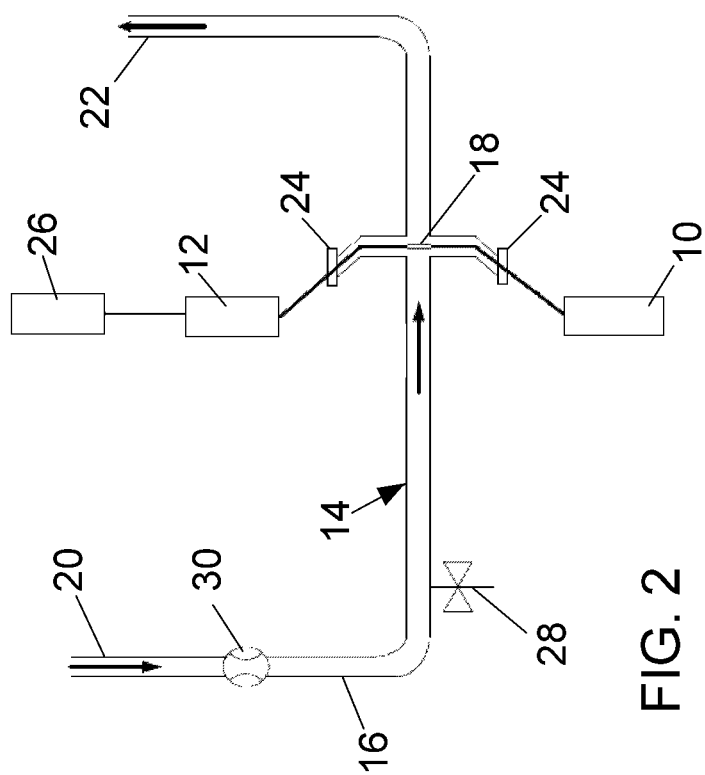

In order to evaluate and characterize the performance of the resulting sensors incorporating the oxazine 170 perchlorate sensing layers, two experimental setups were prepared that each included a light source 10, spectrometer 12, and a water system 14 adapted to contain contaminated water samples for stagnant and dynamic media testing, as schematically represented in FIGS. 1 and 2, respectively. The stagnant water system 14 in FIG. 1 included a test chamber 16 that was sealed with essentially no head space to inhibit volatilization of ammonia gas contained in a stagnant water sample within the chamber 16. In addition, the test chamber 16 was placed on a magnetic stirrer set-up (not shown) to facilitate proper mixing and homogeneity of ammonia in the stagnant water solution.

The water system 14 of the dynamic system of FIG. 2 included a test chamber 16 in the form of a U-shaped piping having a water inlet 20, an outlet 22, and an inlet port 28 through which ammonia was introduced into the system 14. The piping was also provided with a flow meter 30 for monitoring the volumetric flow rate through the chamber 16. The water system 14 of FIG. 2 was fabricated from a polyvinyl chloride (PVC) material representative of piping materials commonly used in residential and commercial building construction. As seen in FIG. 2, an oxazine 170 perchlorate-based sensor 18 was fixtured to be perpendicular to the direction of fluid flow through the chamber 16.

For each of the experimental setups represented in FIGS. 1 and 2, the ammonia introduced was prepared by combining a 28% ammonium hydroxide solution and DI water (greater than 18 MΩ resistance), and the resulting solution was introduced into the chambers 16 at locations of about 22.5 cm from the sensors 18 to ensure sufficient mixing of ammonia with the DI water. The light source 10 employed in each system was an LS-450 blue LED pulsed light source commercially available from Ocean Optics and operated to produce either a pulsed or continuous light output at wavelengths of 470 nm and 550 nm for fluorescence measurements. The spectrometer 12 used to measure the spectra was a high-resolution spectrometer. As represented in FIGS. 1 and 2, each oxazine 170 perchlorate-based sensor 18 was fixtured within the test chamber 16 between POFs that optically connected the sensor 18 to the light source 10 and spectrometer 12 via two SMA connectors 24. The fiber segment of each sensor 18 and its SMA connectors 24 were held in place using epoxy to minimize intensity fluctuation and measurement errors associated with potential unsteadiness of the fiber segment. The spectrometer 12 was connected to a personal computer 26 for automatic recording of changes in optical intensity. The optical intensity and absorbence as a function of wavelength in the presence and absence of contaminants were analyzed with SpectraSuite software. During the investigation, the ammonia detection performances of the sensors 18 were evaluated, including dynamic range, sensitivity, reversibility, and response time. In addition, flow rate for the dynamic water system of FIG. 2 was also recorded.

Based on the construction of the oxazine 170 perchlorate-based sensors 18, three primary phenomena were understood to occur during ammonia sensing: mass diffusion of ammonia vapor from the aqueous testing media through the PDMS membrane layer; a chemical reaction between the diffused ammonia vapor, the water entrapped between the PDMS membrane layer and oxazine 170 perchlorate sensing layer; and intensity modulation due to an evanescent field defined by the fiber segments of the sensors 18. The mass transport of ammonia was driven by a pressure difference between the aqueous testing media and the membrane layer, as well as the difference in concentration.

Figure 3:
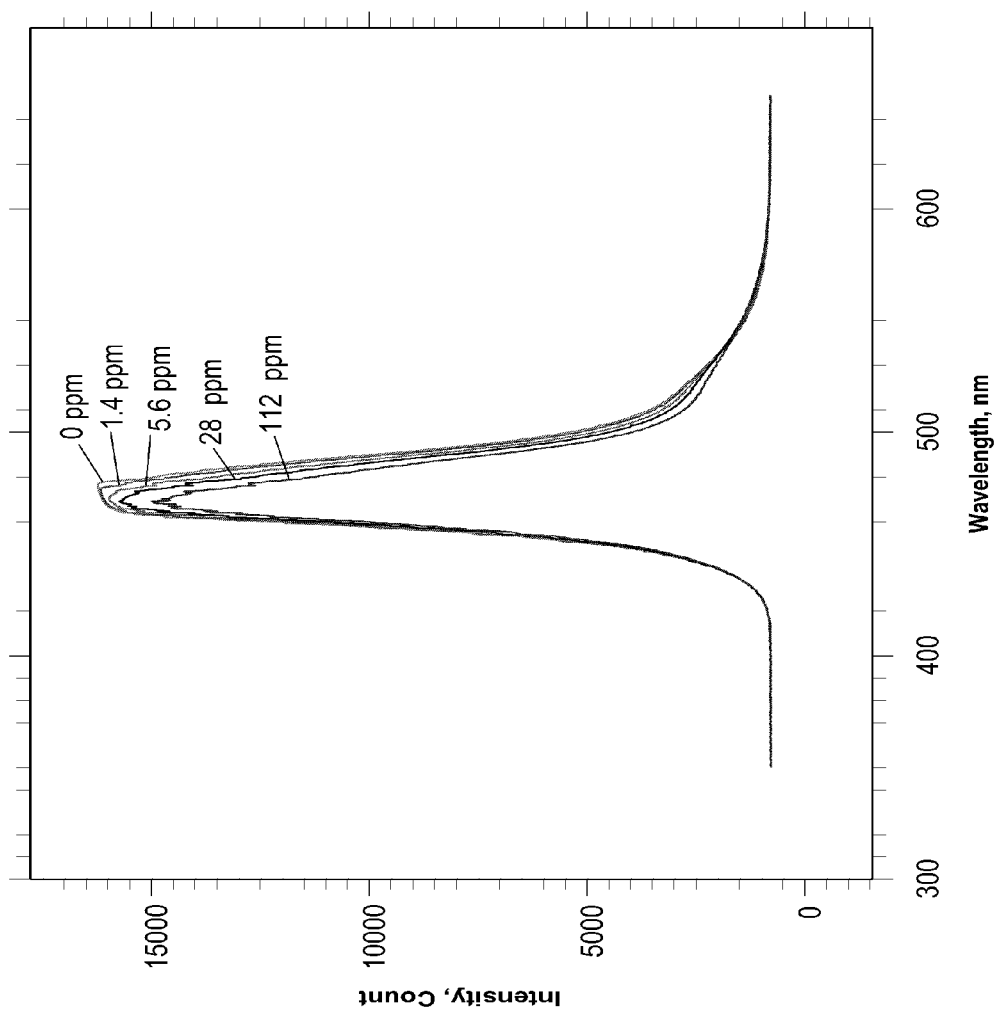
FIG. 3 is a graph plotting intensity versus wavelength of a POF-based sensor exposed to different ammonia concentrations in the stagnant fluid system of FIG. 1.

FIG. 3 presents a typical diagram for intensity as a function of wavelength for various ammonia concentrations investigated with the stagnant system of FIG. 1. The reference intensity is referred to as 0 ppm. From FIG. 3, it can be observed that there was a distinct peak of intensity at a wavelength of about 476.74 nm (112 ppm). The intensity decreased with the increase in ammonia concentration, indicating that the absorbence of the sensor 18 increased with an increase in ammonia concentration as the absorbance is related to intensity according to Equation 4:

$$A = -\log_{10}(I/I_0) \quad (4)$$

where I is the intensity of light at a specified wavelength λ that has passed through a sample (transmitted light intensity) and $I_0$ is the intensity of the light before it enters the sample or incident light intensity.

Figure 4:
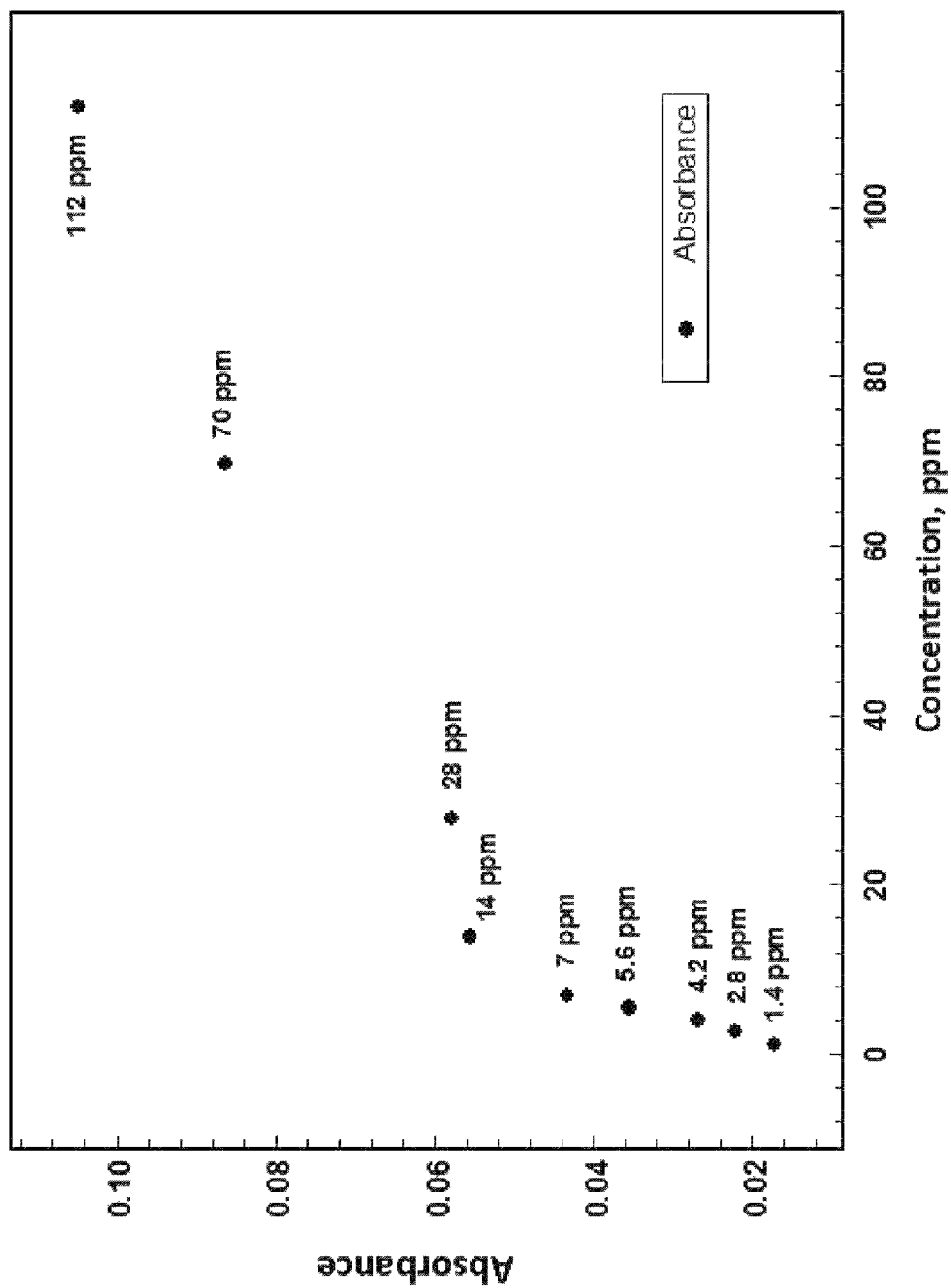
FIG. 4 is a graph plotting absorbance versus ammonia concentration of the POF-based sensor in the stagnant fluid system of FIG. 1.

FIG. 4 depicted the calculated absorbence of the sensor 18 evaluated in the stagnant system of FIG. 1 at various ammonia concentrations based on Eq. (4). $NH_3$ concentrations ranged from 0 to 112 ppm. FIG. 4 suggests the existence of three absorbance regimes: 0≤C≤14 ppm, 14≤C≤28 ppm, and 28≤C≤112 ppm. In addition, two near-linear absorbance response regimes can be observed in FIG. 4, 0≤C≤14 ppm and 14≤C≤28 ppm, which is consistent with the Beer-Lambert law, A=εlC, where ε is the molar absorptivity of the absorber, l is the path length, and C is the concentration of the reacting products of absorbing material and contaminants. However, in the middle range for ammonia concentration (14≤C≤28 ppm), the change in absorbance with increase in ammonia concentration was almost negligible. This may have been attributable to a negligible pressure and concentration difference across the PDMS membrane layer in this concentration range.

From FIG. 4, it should also be noted that during the early stage of the sensing process, a change in concentration of 12.6 ppm (from 1.4 to 14 ppm) resulted in a change in absorbance of 4%, and a change in concentration of about 42 ppm (from 28 to 70 ppm) resulted in only an approximately 3% change in absorbance. A further increase in concentration of 42 ppm (from 70 to 112 ppm) resulted in an even smaller change in absorbance (about 2%). This phenomenon suggested that the sensors constructed for the investigation would be most sensitive at low ammonia concentrations.

Figure 5:
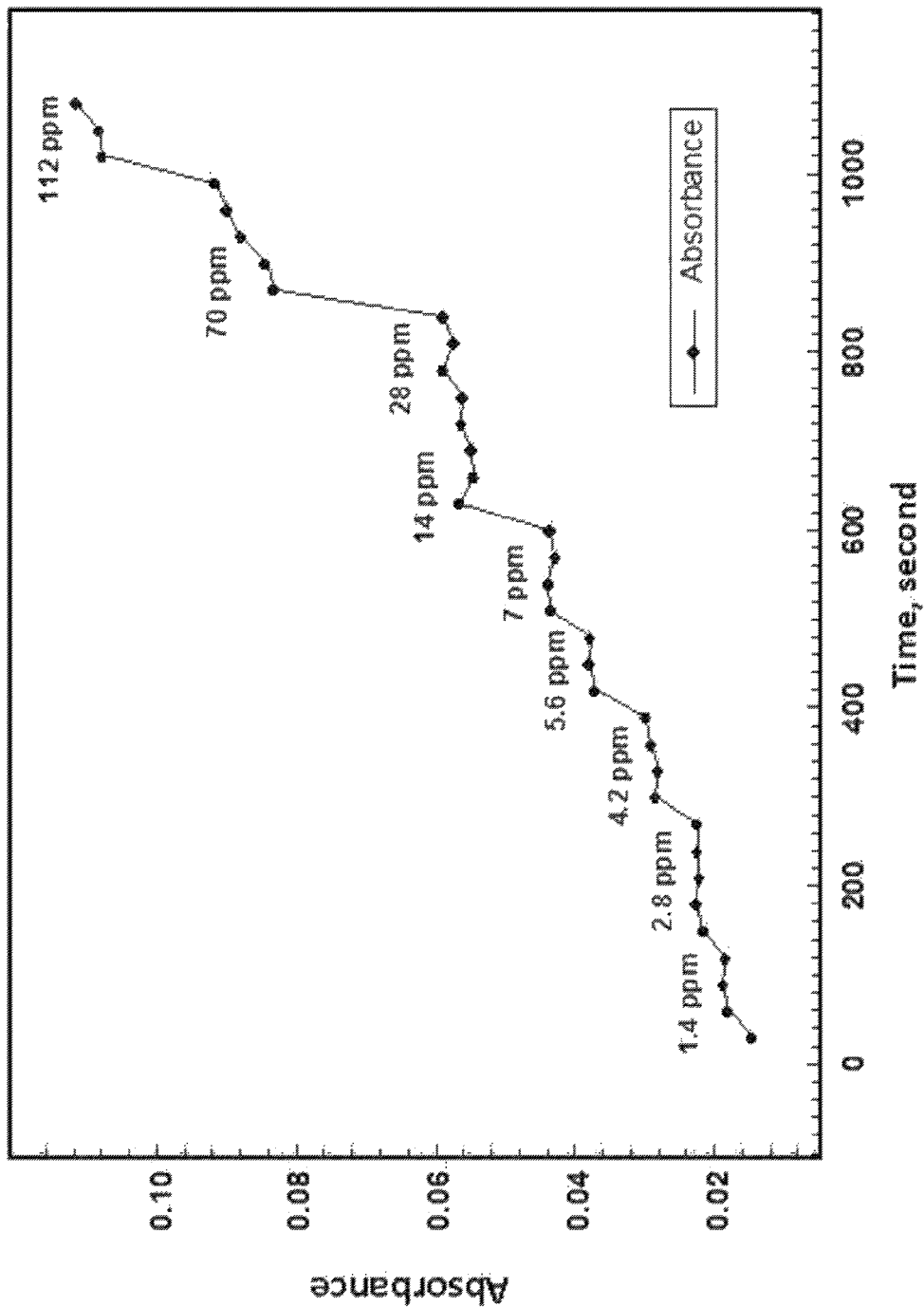
FIG. 5 is a graph plotting absorbance versus time of the POF-based sensor in the stagnant fluid system of FIG. 1 when subjected to batch additions of ammonia to increase ammonia concentration.

FIG. 5 illustrates absorbance as a function of time for various concentrations at 476.74 nm wavelength. During this phase of the investigation, the sensor 18 was first placed in DI water, and then known volumes of concentrated ammonia hydroxide solution were added to the DI water sequentially with each addition being spaced from another to allow for equilibration. FIG. 5 evidences that the response of the sensor 18 at higher ammonia concentrations (such as 112 ppm) was much faster than at lower ammonia concentrations (such as 1.4 ppm or 2.8 ppm). This observation was explained on the basis that the driving force (concentration and pressure gradients) for ammonia diffusion through the PDMS membrane layer would be greater at higher concentrations.

Figure 6:
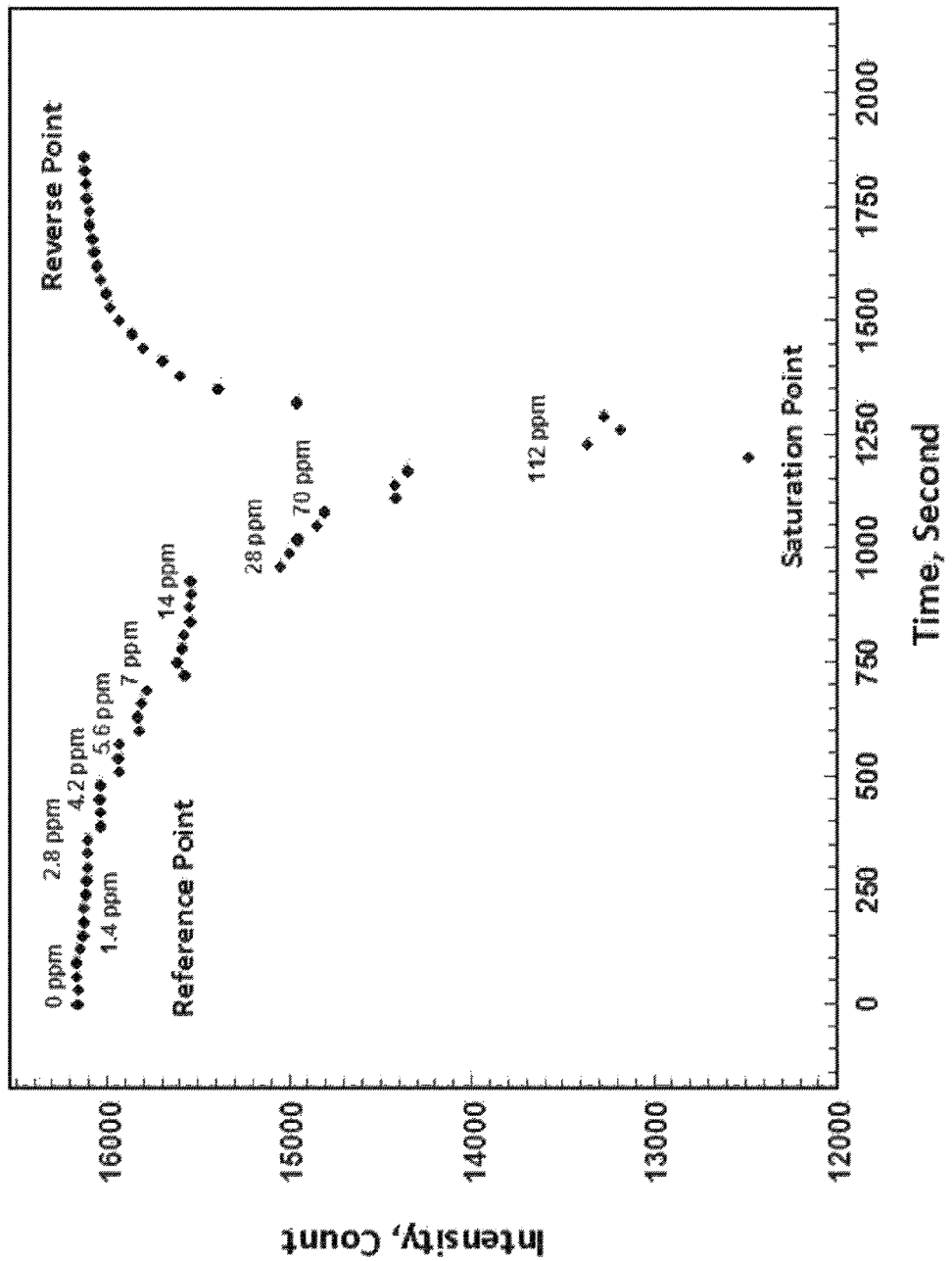
FIG. 6 is a graph plotting intensity versus time of the POF-based sensor in the stagnant fluid system of FIG. 1 when subjected to batch additions of ammonia to increase ammonia concentration, and further plots data evidencing the reversibility of the POF-based sensor.

FIG. 6 plots the results of two sets of tests: one was a sensitivity test to study the sensor response to changes in concentration, and the other was a reversibility test. The initial optical intensity was measured in DI water in the absence of ammonia contaminant, and is referred to in FIG. 6 as a reference point of 0 ppm. This measurement was followed by additions of ammonia at concentrations ranging from 1.4 ppm to 112 ppm, at which the corresponding change in intensity was recorded. At a given ammonia concentration, intensity was recorded when two consecutive measurements exhibited a negligible change. At the end of the sensitivity test, additions of DI water were made to evaluate the reversibility (hysteresis) characteristics of the sensor 18.

During this investigation, the sensor 18 responded to the changes in ammonia concentration almost instantaneously, typically within 10 seconds. Over 25% intensity changes were observed (from 16241 counts for 0 ppm to 12000 counts for 112 ppm, respectively). After the maximum ammonia concentration of 112 ppm had been tested, the sensor was placed in fresh DI water. The optical intensity immediately started to increase and within around 10 minutes it had nearly returned to its original value of 16241 counts, evidencing a 99.6% reversibility. From these results, it was concluded that the structure of the sensor 18 had enabled a fast mass diffusion of ammonia both in or out through the PDMS membrane layer, resulting in excellent reversibility.

The performance of the sensor 18 in the dynamic water system of FIG. 2 was then investigated. Under flowing water conditions, ranging from about 55 ml/s to about 65 ml/s, the sensor 18 was evaluated for sensitivity, reversibility, response and reverse time, and durability. Sensitivity indicates how much the sensor's intensity varied with ammonia concentration or its ability to respond to ammonia contaminant. Prior to conducting the evaluation, a baseline optical intensity of the sensor 18 was measured in a municipal flowing water environment. The maximum reference intensity was 16200 counts at a wavelength of 478.31 nm. This peak intensity would change according to ammonia concentration. Seven concentrations of ammonia hydroxide solution (250, 125, 62.5, 31.25, 15.63, 7.8, and 3.9 ppm) were injected into a municipal source of water, starting with the highest to the lowest concentration, to study sensor properties.

Figure 7:
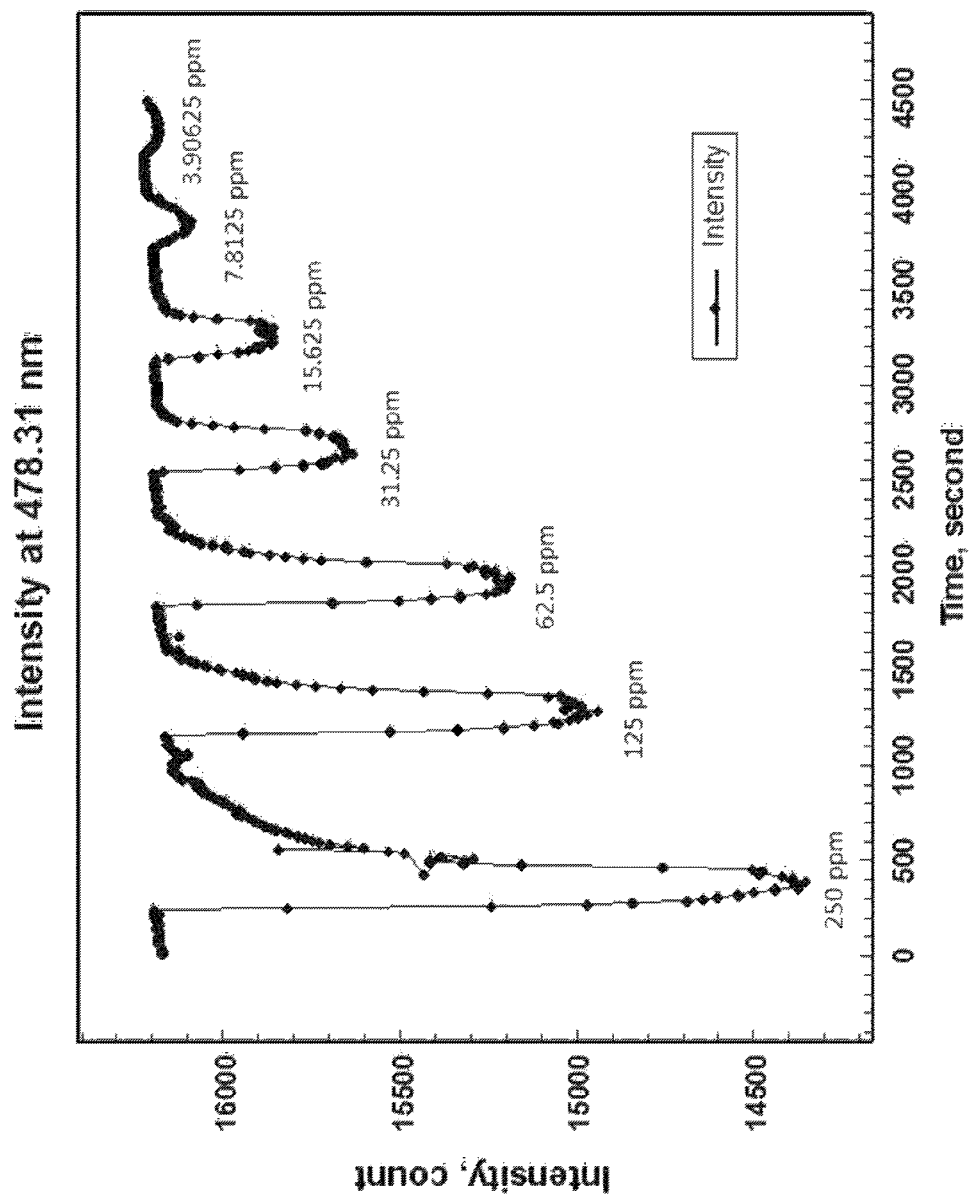
FIG. 7 is a graph plotting intensity versus time of a POF-based sensor exposed to different ammonia concentrations in the dynamic fluid system of FIG. 2.
Figure 8:
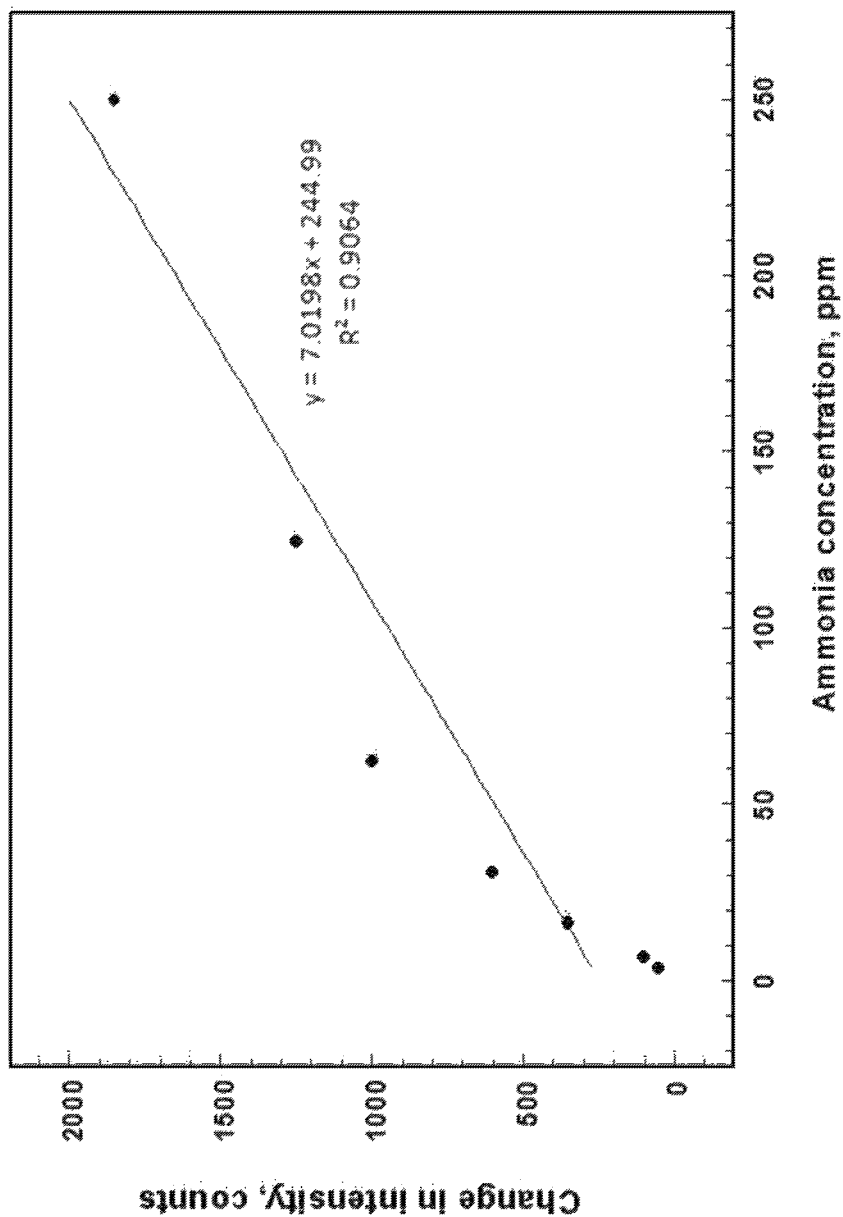
FIG. 8 is a graph plotting intensity versus ammonia concentration of the POF-based sensor in the dynamic fluid system of FIG. 2.

FIG. 7 represents intensity as a function of ammonia concentration at a wavelength of 478.31 nm. From FIG. 7, it can be seen that the change in intensity, $\Delta I$, decreased with decreasing ammonia concentration. To further clarify this phenomenon, data from FIG. 7 was used to plot the variation of intensity with concentration, plotted in FIG. 8. The change in intensity is linearly related to concentration according to the relation, $\Delta I=\beta C+\gamma$, where $\beta=7$ and $\gamma=245$ for this study. The values of $\beta$ and $\gamma$ were dependent on the type of contaminant, whereas the sensing material, thickness of the sensing layer, etc., were constants.

Figure 9:
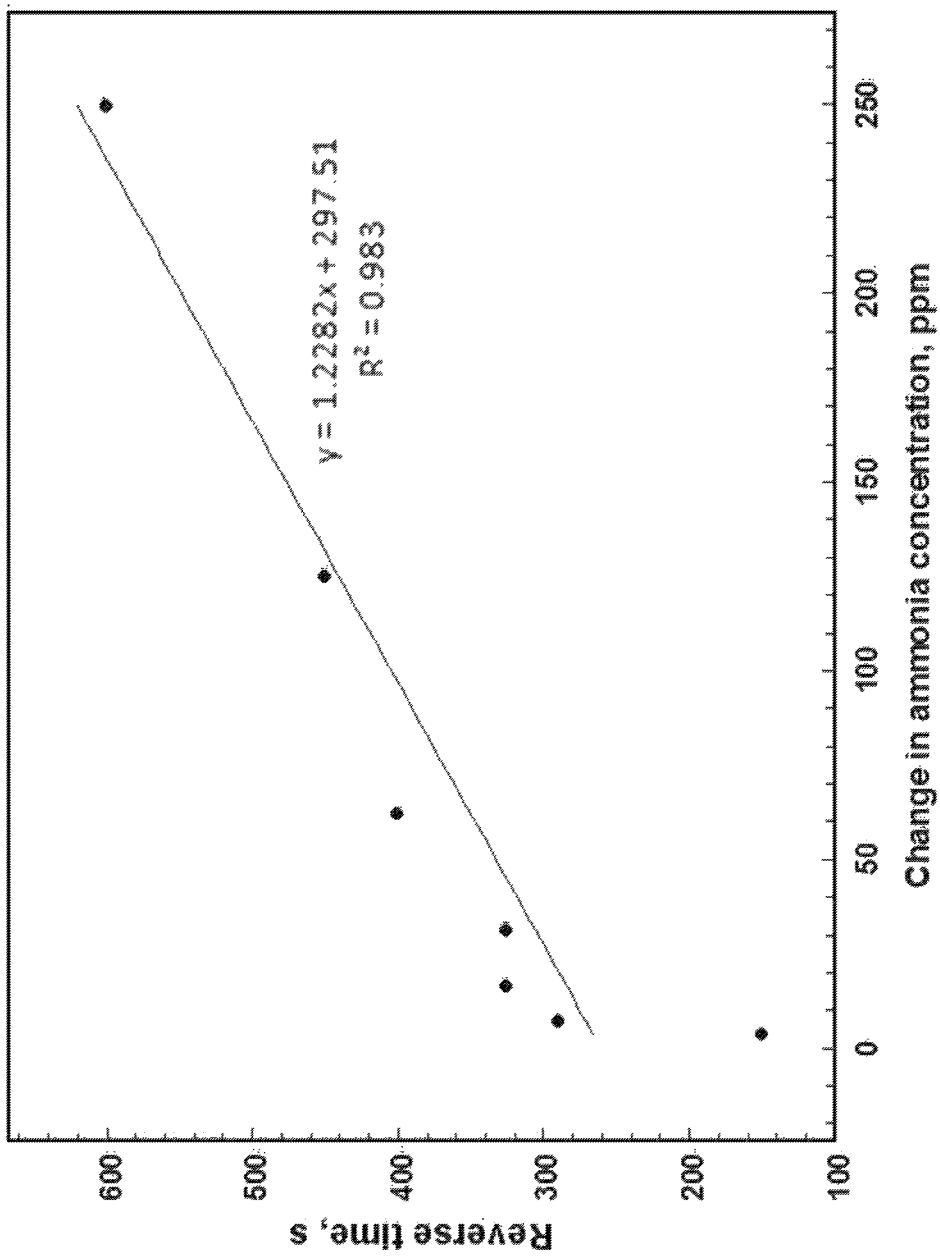
FIG. 9 is a graph plotting reverse time versus change in ammonia concentration for the POF-based sensor in the dynamic fluid system of FIG. 2.

The presence of ammonia contaminant in water changes the reference intensity value, $I_{ref}$ to $I_f$, where the subscripts "ref" and "f" refer to the reference and final intensity readings, respectively. Reversibility is referred to as the ability of the sensor 18 to reverse to its reference intensity in the absence of ammonia contaminant and is quantified as $(I_{ref}/I_{final})\times 100\%$. FIG. 7 showed that over the range of ammonia concentrations evaluated, the sensor was 99.7% reversible. Using data from FIG. 7, the reverse time is presented in FIG. 9 as a function of concentration. It is noted that the reversibility time is a linear function of concentration and is correlated by $t_R \approx \alpha C+\delta$, where $\alpha=1.23$ and $\delta=829$ for this study. The reverse time increased with concentration. At high concentrations of ammonium hydroxide solution, it was expected that more ammonia vapor would diffuse through the PDMS membrane layer into the sensing layer. Therefore, more time would be needed for ammonia vapor to diffuse from the sensing layer to the surrounding water.

Figure 10:
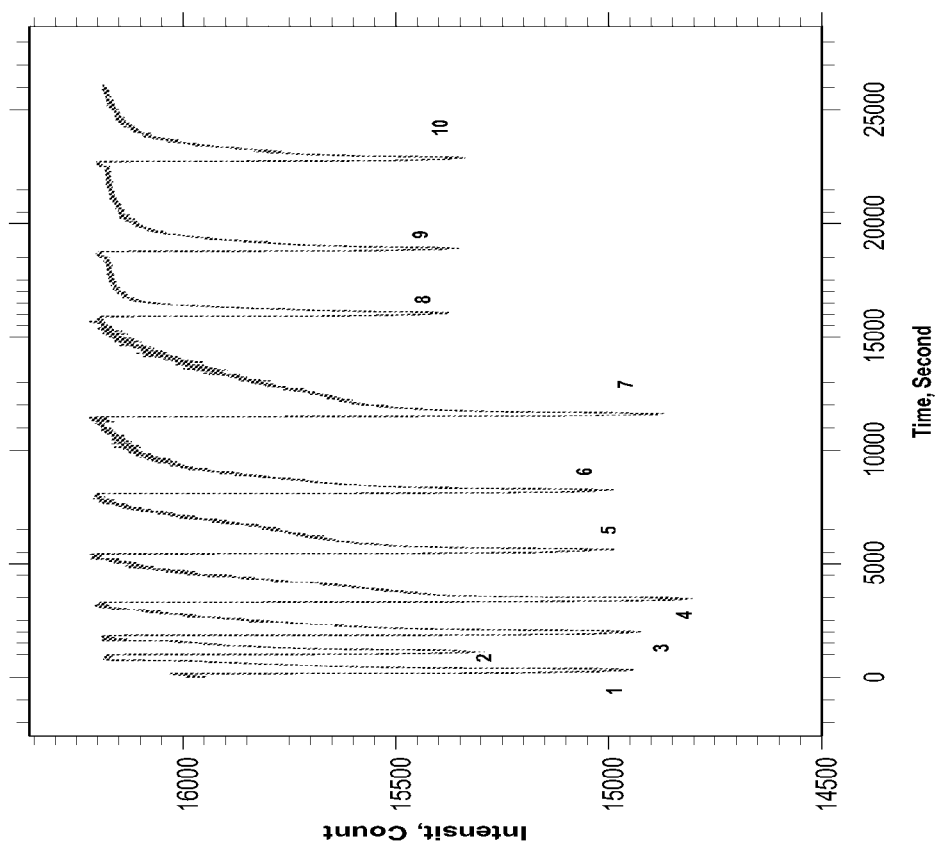
FIG. 10 is a graph plotting intensity over time of the POF-based sensor when subjected to changes in ammonia concentration in the dynamic fluid system of FIG. 2.

The basic difference between the stagnant and dynamic water systems of FIGS. 1 and 2 was the dynamic flow of the contaminated water. In order to elucidate the effect of water flow rate on sensor response, the sensor 18 in the flowing water distribution system of FIG. 2 was evaluated over a period of ten days at a constant ammonia concentration of 125 ppm. The volumetric flow rates during the first seven days and the last three days were 54.34 ml/s and 65.36 ml/se, respectively. A measured volume of concentrated ammonia hydroxide solution was added into flowing water daily. The ammonia concentration was calculated based on the volume ratio of the ammonium hydroxide to the volume of the testing chamber. The volume of the ammonium hydroxide solution was adjusted accordingly to ensure that the same ammonia concentration, 125 ppm, was tested. It could be observed in FIG. 10 that for each flow rate the sensor responded with similar optical intensity output, though the larger flow rate resulted in a smaller change in intensity even though the same ammonia concentration was tested. This observation was in agreement with the hypothesis that higher water flow rates would reduce the contact time of ammonia with the sensing element and hence result in a weaker response. For practical application, the range of flow rate over which the sensor is sensitive could be specified.

Figure 11:
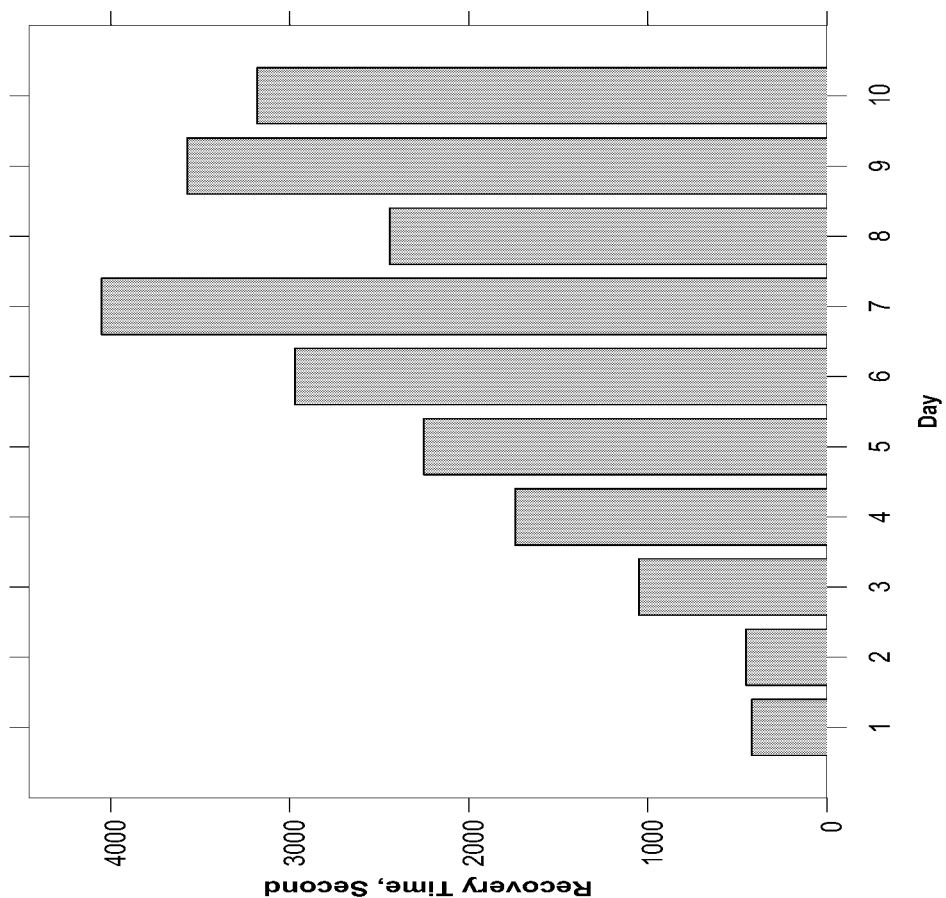
FIG. 11 is a bar graph indicating the recovery time of the POF-based sensor based on the data of FIG. 10.

Another phenomenon that was observed was that as the testing time of the sensor 18 increased (in days), the time required for the sensor 18 to return to its original state (reverse time) was prolonged. FIG. 11 depicts this phenomenon, in which the 99% recovery time (in terms of intensity) for the 10-day running water testing is plotted against test days. The first seven days (tested at the lower flow rate) showed a substantial increasing trend and the recovery time increased from less than ten minutes for the first day to over sixty minutes for the seventh day. This increasing recovery time may be attributed to the hypothesis that water molecules might have been carried by the ammonia vapor and penetrated the membrane layer. As a result of this increase in the water molecules, it would take longer time for ammonia to completely diffuse out of the sensor 18. This slowed ammonia outward diffusion resulted in slower recovery and hence prolonged recovery time.

The results of the evaluations performed on the sensors 18 are summarized in Table 1 below for both the stagnant and dynamic water conditions. Table 1 compares the response time, minimal detection limit and reversibility, and evidences that the performances of the sensors 18 were similar for the two different testing setups. In particular, the sensor 18 exhibited excellent ammonia sensing capability under stagnant water testing conditions. While similar excellent responses to the change of ammonia concentration were observed under dynamic testing conditions, flow rate was observed to have an influence on recovery time as a function of deployment time (in days).

TABLE 1

| System (Water) | Response Time | Minimum Detection | Reversibility |
|---|---|---|---|
| Stagnant | Instantaneous | 1.4 ppm | 99% |
| Dynamic | Instantaneous | 3.9 ppm | 99% |

From the investigation reported above, it was concluded that an oxazine 170 perchlorate based POF opto-chemical sensor could be constructed to include an entrapped moisture layer between the oxazine 170 perchlorate-based layer and a suitable membrane layer, such as that provided by the PDMS layer used in the investigation.

While the invention has been described in terms of a specific embodiment, it is apparent that other forms could be adopted by one skilled in the art. Therefore, the scope of the invention is to be limited only by the following claims.

The invention claimed is:

1. An opto-chemical sensor configured to detect at least one contaminant in a fluid within a fluid system, the sensor comprising:
    a polymer optical fiber;
    a sensing layer comprising oxazine 170 perchlorate on the polymer optical fiber;
    a membrane layer on the sensing layer, the membrane layer being gas permeable and not permeable to the fluid in the fluid system; and
    moisture entrapped by and between the sensing and membrane layers.

2. The opto-chemical sensor according to claim 1, wherein the sensing layer consists of oxazine 170 perchlorate.

3. The opto-chemical sensor according to claim 1, wherein the membrane layer comprises a silicone elastomer.

4. The opto-chemical sensor according to claim 1, wherein the membrane layer comprises polydimethylsiloxane.

5. The opto-chemical sensor according to claim 1, wherein the membrane layer consists of polydimethylsiloxane.

6. The opto-chemical sensor according to claim 1, wherein the polymer optical fiber comprises poly(methyl methacrylate).

7. The opto-chemical sensor according to claim 1, wherein the sensor is installed in a fluid system for detecting at least one contaminant in a stagnant fluid within the fluid system.

8. The opto-chemical sensor according to claim 1, wherein the sensor is installed in a fluid system for detecting at least one contaminant in a fluid flowing in the fluid system.

9. A method of using the opto-chemical sensor according to claim 1, the method comprising:
    installing the sensor in a fluid system containing a fluid; and
    detecting a level of a contaminant in the fluid.

10. The method according to claim 9, wherein the fluid is stagnant within the fluid system.

11. The method according to claim 9, wherein the fluid is flowing through the fluid system.

12. The method according to claim 9, wherein the contaminant is ammonia.

13. The method according to claim 9, wherein the fluid is water.

14. A method of fabricating an opto-chemical sensor configured to detect at least one contaminant in a fluid within a fluid system, the method comprising:
    depositing a sensing layer on a polymer optical fiber, the sensing layer comprising oxazine 170 perchlorate; and
    depositing a membrane layer on the sensing layer so as to entrap moisture therebetween, the membrane layer being gas permeable and not permeable to the fluid in the fluid system.

15. The method according to claim 14, wherein the sensing layer consists of oxazine 170 perchlorate.

16. The method according to claim 14, wherein the moisture is entrapped between the membrane layer and the sensing layer by exposing the sensing layer to water prior to the step of depositing the membrane layer.

17. The method according to claim 14, further comprising removing a portion of a cladding layer of the polymer optical fiber to expose a polymer core thereof, wherein the sensing layer is directly deposited on the polymer core.

18. The method according to claim 17, wherein the polymer core comprises poly(methyl methacrylate).

19. The method according to claim 17, further comprising polishing the polymer core prior to depositing the sensing layer thereon.

20. The method according to claim 14, wherein the membrane layer is permeable to ammonia and impermeable to water.

* * * * *